(12) United States Patent
Kobayashi et al.

(10) Patent No.: US 10,117,619 B2
(45) Date of Patent: Nov. 6, 2018

(54) OPTICAL SENSOR

(71) Applicant: NIHON KOHDEN CORPORATION, Tokyo (JP)

(72) Inventors: Naoki Kobayashi, Tokyo (JP); Teiji Ukawa, Tokyo (JP); Kazumasa Ito, Tokyo (JP); Masahiro Takeuchi, Tokyo (JP); Yoshinori Ueda, Tokyo (JP); Hiroko Hagiwara, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 602 days.

(21) Appl. No.: 14/558,215

(22) Filed: Dec. 2, 2014

(65) Prior Publication Data
US 2015/0157264 A1 Jun. 11, 2015

(30) Foreign Application Priority Data
Dec. 11, 2013 (JP) .................................. 2013-256408

(51) Int. Cl.
*A61B 5/1455* (2006.01)
*A61B 5/00* (2006.01)

(52) U.S. Cl.
CPC .......... *A61B 5/6826* (2013.01); *A61B 5/0013* (2013.01); *A61B 5/14552* (2013.01); *A61B 5/6831* (2013.01); *A61B 5/6838* (2013.01); *A61B 5/6843* (2013.01); *A61B 5/72* (2013.01); *A61B 5/7405* (2013.01); *A61B 2503/045* (2013.01); *A61B 2560/0425* (2013.01)

(58) Field of Classification Search
CPC . A61B 5/02416; A61B 5/1455; A61B 5/6826; A61B 5/6825; A61B 5/6831; A61B 5/14551; A61B 5/14552; A61B 5/7405
See application file for complete search history.

(56) References Cited

U.S. PATENT DOCUMENTS

| | | | |
|---|---|---|---|
| 5,522,388 A | 6/1996 | Ishikawa et al. | |
| 6,230,035 B1 * | 5/2001 | Aoyagi | A61B 5/14551 600/310 |
| 6,353,750 B1 * | 3/2002 | Kimura | A61B 5/0031 600/310 |
| 6,571,114 B1 | 5/2003 | Koike et al. | |

(Continued)

FOREIGN PATENT DOCUMENTS

| | | |
|---|---|---|
| CN | 1316888 A | 10/2001 |
| CN | 102525444 A | 7/2012 |

(Continued)

OTHER PUBLICATIONS

The extended European Search Report for the related European Patent Application No. 14196029.4 dated May 19, 2015.
Japanese Office Action issued in Patent Application No. JP-2013-256408 dated Feb. 21, 2017.
Japanese Office Action issued in Patent Application No. JP 2013-256408 dated Sep. 26, 2017.

(Continued)

*Primary Examiner* — Eric Winakur
(74) *Attorney, Agent, or Firm* — Pearne & Gordon LLP

(57) ABSTRACT

An optical sensor includes: a light emitter; a light receiver; a rod-shaped grasping member in which one of the light emitter and the light receiver is disposed, and which is to be grasped by a hand of a subject; and a clamping member which is adapted to clamp a part of the hand of the subject with the grasping member, another one of the light emitter and the light receiver being disposed in the clamping member.

17 Claims, 10 Drawing Sheets

(56) References Cited

U.S. PATENT DOCUMENTS

| | | | |
|---|---|---|---|
| 6,850,788 B2 * | 2/2005 | Al-Ali | A61B 5/14552 600/323 |
| 8,135,447 B2 * | 3/2012 | Kondoh | A61B 5/0059 600/310 |
| 2003/0100840 A1 | 5/2003 | Sugiura et al. | |
| 2003/0181799 A1 | 9/2003 | Lindekugel et al. | |
| 2003/0229276 A1 | 12/2003 | Sarussi et al. | |
| 2007/0049813 A1 * | 3/2007 | Blouin | A61B 5/14552 600/310 |
| 2009/0163787 A1 * | 6/2009 | Mannheimer | A61B 5/14552 600/324 |
| 2009/0227852 A1 | 9/2009 | Glaser | |
| 2011/0224518 A1 | 9/2011 | Tindi et al. | |
| 2012/0059233 A1 * | 3/2012 | Huber | A61B 5/6826 600/323 |
| 2012/0130211 A1 | 5/2012 | Kobayashi et al. | |
| 2013/0091642 A1 | 4/2013 | Dykes et al. | |
| 2014/0088396 A1 | 3/2014 | Shimuta | |

FOREIGN PATENT DOCUMENTS

| | | |
|---|---|---|
| EP | 1 859 735 A1 | 11/2007 |
| JP | H06-032273 A | 2/1994 |
| JP | 3345481 B2 | 11/2002 |
| JP | 2005-525852 A | 9/2005 |
| JP | 3896408 B2 | 3/2007 |
| JP | 2007-289462 A | 11/2007 |
| JP | 2007-289463 A | 11/2007 |
| JP | 2009-226182 A | 10/2009 |
| JP | 2012-254194 A | 12/2012 |
| WO | 2010/011763 A1 | 1/2010 |
| WO | 2012/165064 A1 | 12/2012 |

OTHER PUBLICATIONS

Chinese Office action issued in Patent Application No. CN-201410734137.X dated Sep. 7, 2018.

* cited by examiner

OPTICAL SENSOR

CROSS-REFERENCE TO RELATED APPLICATION(S)

This application is based upon and claims the benefit of priority from prior Japanese patent application No. 2013-256408, filed on Dec. 11, 2013, the entire contents of which are incorporated herein by reference.

BACKGROUND

The presently disclosed subject matter relates to an optical sensor, and particularly to an optical sensor to be used in pulse oximetry for a neonate.

There is a pulse oximetry which is a technique for noninvasively measuring the arterial oxygen saturation which is one of indexes showing the condition of the subject. Pulse oximetry is performed by attaching an optical sensor including a light emitter and a light receiver, to, for example, the fingertip of the hand of the subject (for example, see Japanese Patent No. 3,896,408).

Since the fingertip of the hand of a neonate is very small, it is difficult to attach an optical sensor including a light emitter and a light receiver, to the fingertip. Therefore, a measurement is sometimes performed while an optical sensor is attached to the wrist or the palm. In the wrist, however, there are bones, and an abundant capillary bed does not exist unlike the fingertip, so that a measurement error is large. In the palm, by contrast, a gap tends to be formed between the skin surface and an optical sensor in accordance with a grasping motion due to the grasp reflex or the like, and therefore a measurement error is large.

SUMMARY

The presently disclosed subject matter may provide a technique for, even in the case where the subject of pulse oximetry is a neonate, suppressing a measurement error from occurring.

There may be provided an optical sensor comprising: alight emitter; a light receiver; and a rod-shaped grasping member in which the light emitter and the light receiver are disposed, and which is to be grasped by a hand of a subject.

There may be also provided an optical sensor comprising: a light emitter; a light receiver; a rod-shaped grasping member in which one of the light emitter and the light receiver is disposed, and which is to be grasped by a hand of a subject; and a clamping member which is adapted to clamp a part of the hand of the subject with the grasping member, another one of the light emitter and the light receiver being disposed in the clamping member.

The optical sensor may further comprise: a scattering layer which is placed in an optical path of light emitted from the light emitter.

The light emitter may be placed so that emitted light passes through a plurality of fingers of the subject.

The optical sensor may further comprise: a light shielding member which is disposed between the plurality of fingers.

The optical sensor may further comprise: a belt member, one end of the belt member may be fixed to one of the grasping member and the clamping member, and a part of the belt member may be attachable to and detachable from the other of the grasping member and the clamping member.

The part of the belt member may be variable.

The grasping member may have a shape of a rotating body.

A positional relationship between the light emitter and the light receiver may be constant.

At least a part of the grasping member may be flexible.

The grasping member may include a first portion in which at least a thumb and index finger of the subject are to be placed, and a second portion in which at least one of the light emitter and the light receiver is disposed, the first portion may be higher in rigidity than the second portion, and the second portion may be higher in flexibility than the first portion.

An outer circumferential surface of the grasping member may include a recess having a shape which is adapted to receive a part of a right hand of the subject.

The optical sensor may further comprise: an indicator guiding grasping by the right hand of the subject.

The optical sensor may further comprise: a sensor which is configured to detect a state change of at least a part of the grasping member, the change being due to a grasping pressure exerted by the subject.

The optical sensor may further comprise: a sound outputting section which is configured to output predetermined sound.

The optical sensor may further comprise: a wireless communicating section which is configured to transmit and receive a signal between the light emitter and the light receiver, and an external apparatus.

The optical sensor may further comprise: a calculating section which is configured to perform a calculation process on a signal communicated between the light emitter and the light receiver, and the wireless communicating section.

The light emitter and the light receiver may be supported by a member having a light shielding property.

DETAILED DESCRIPTION OF EXEMPLARY EMBODIMENTS

Figure 1A:
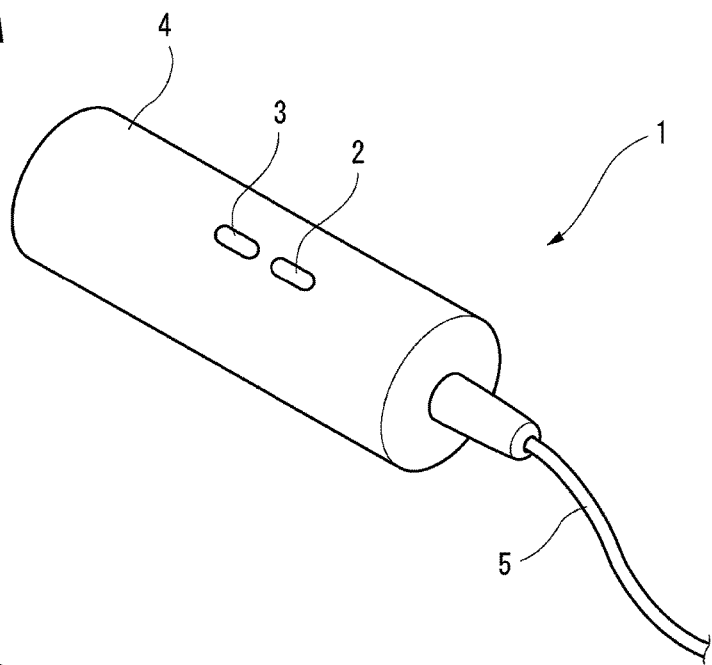
FIGS. 1A and 1B are views showing an optical sensor of a first embodiment of the presently disclosed subject matter.

Embodiments of the presently disclosed subject matter will be described in detail with reference to the accompanying drawings. In the drawings which will be used in the following description, the scale is adequately changed in order to draw components in a recognizable size.

FIG. 1A shows an optical sensor 1 of a first embodiment of the presently disclosed subject matter. The optical sensor 1 includes a light emitter 2, a light receiver 3, a grasping member 4, and a cable 5. The cable 5 is connected to a measuring apparatus which is not shown. An example of the measuring apparatus is a pulse oximeter. In this case, the optical sensor 1 is used as a probe for pulse oximetry.

Figure 1B:
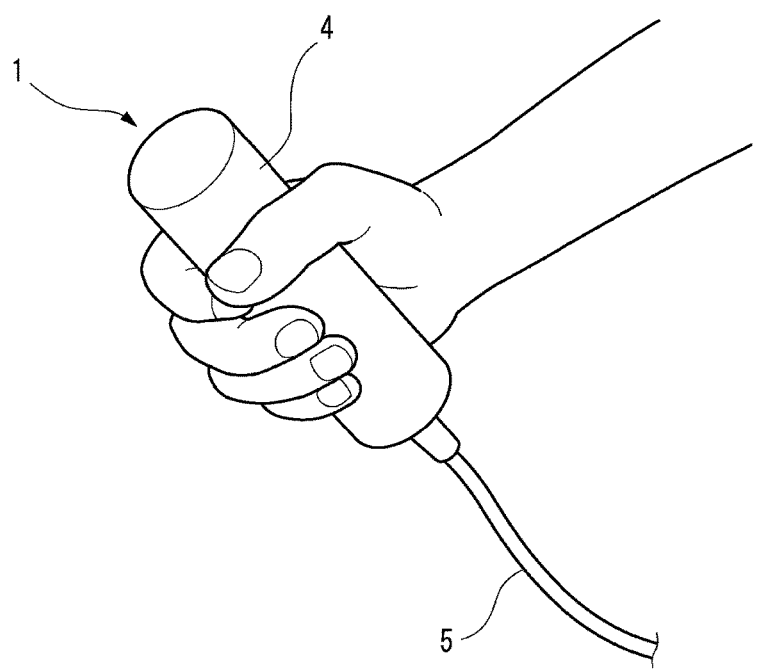

As shown in FIG. 1B, the grasping member 4 has a rod-like shape which is to be grasped by the subject. The light emitter 2 and the light receiver 3 are disposed in the grasping member 4. In the outer circumferential surface of the grasping member 4 which is curved, the light emitting surface of the light emitter 2 and the light receiving surface of the light receiver 3 are directed to the outside. The light emitter 2 and the light receiver 3 are placed at positions which are opposed to the palm of the subject in a state where the grasping member is grasped by the subject. The placement of the light emitter 2 and the light receiver 3 may be reversed.

Based on a control signal input from the measuring apparatus via the cable 5, the light emitter 2 emits a red light beam and an infrared light beam. The light receiver 3 outputs a signal according to the intensities of the light beams which are reflected from the palm of the subject. The signal is supplied to the measuring apparatus via the cable 5.

In hemoglobin in blood, absorbances of a red light beam and an infrared light beam are different from each other depending on presence or absence of oxygenation. When the intensities of the light beams detected by the light receiver 3 are analyzed, therefore, it is possible to measure the arterial oxygen saturation (SpO2). When the pulse wave component due to the pulsation of the heart is detected, it is possible to measure the heart rate.

According to the configuration, a gap is hardly formed between the outer circumferential surface of the grasping member 4 which is curved, and the palm of the subject, and the contactness of the light emitter 2 and the light receiver 3 with the palm is enhanced. When the grasping member 4 is grasped by aggressively using the grasp reflex which can be observed in a neonate, particularly, the contactness is further enhanced. Even in the case where the subject of pulse oximetry is a neonate, therefore, it is possible to suppress a measurement error from occurring.

Figure 2A:
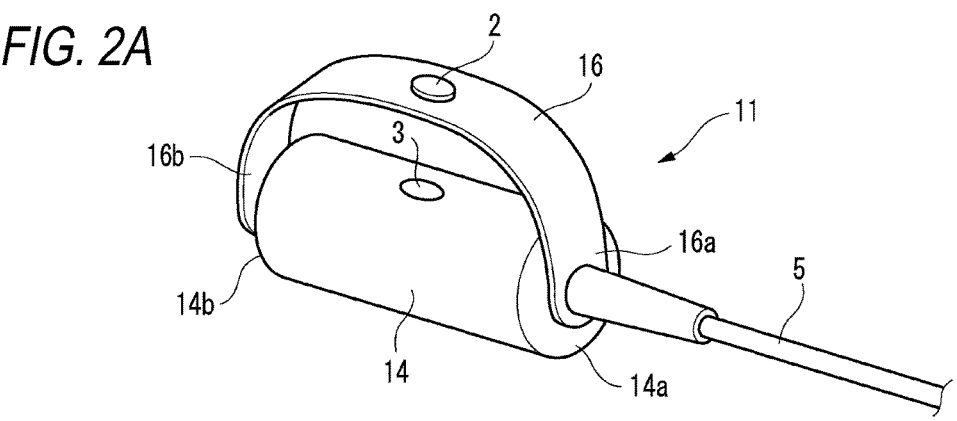
FIGS. 2A to 2C are views showing an optical sensor of a second embodiment of the presently disclosed subject matter.

FIG. 2A shows an optical sensor 11 of a second embodiment of the presently disclosed subject matter. The components which are substantially identical to those of the optical sensor 1 of the first embodiment are denoted by the same reference numerals, and repeated description is omitted. The optical sensor 11 includes the light emitter 2, the light receiver 3, a grasping member 14, the cable 5, and a strap 16 (an example of the clamping member).

The grasping member 4 has a rod-like shape which is to be grasped by the subject. The light receiver 3 is disposed in the grasping member 14. In the outer circumferential surface of the grasping member 14 which is curved, the light receiving surface of the light receiver 3 is directed to the outside.

The strap 16 extends in the longitudinal direction of the grasping member 14. A first end portion 16a of the strap 16 is fixed to a first end portion 14a in the longitudinal direction of the grasping member 14. A second end portion 16b of the strap 16 is attachable to and detachable from a second end portion 14b in the longitudinal direction of the grasping member 14. The light emitter 2 is placed on the strap 16.

Figure 2B:
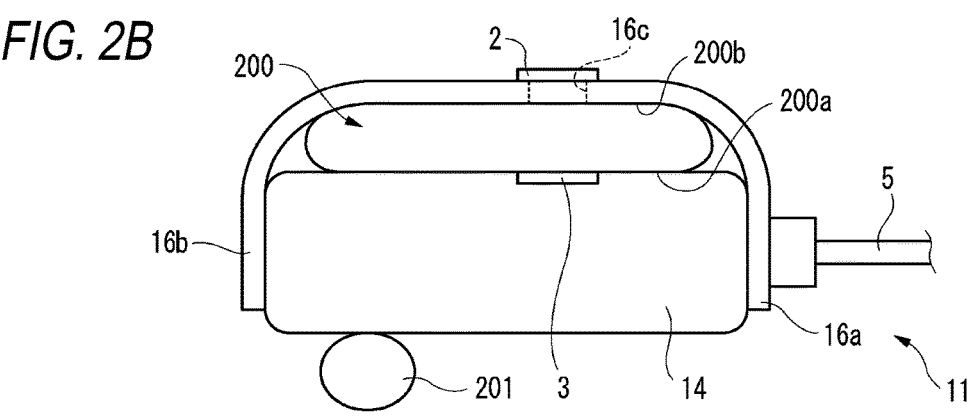

FIG. 2B shows a state where the grasping member 14 is grasped by the subject. The reference numeral 200 denotes a section of the hand of the subject, 200a denotes the palm of the subject, 200b denotes the back of the hand of the subject, and 201 denotes a section of the thumb of the subject. In a state where the grasping member 14 is grasped by the hand 200 of the subject, namely, the strap 16 cooperates with the grasping member 14 to clamp a part of the hand 200 of the subject.

An opening 16c is formed in the strap 16. The light emitter 2 is placed so as to cover the opening 16c. In a state where the second end portion 16b of the strap 16 is fixed to the grasping member 14, the light emitting surfaces of the light emitter 2 is opposed to the outer circumferential surface of the grasping member 14 through the opening 16c. Namely, the light emitter 2 and the light receiver 3 are placed respectively at positions which are opposed to each other across the hand 200 of the subject in a state where the hand 200 is clamped between the strap 16 and the grasping member 14.

The red and infrared light beams emitted from the light emitter 2 enter the back 200b of the hand through the opening 16c. The light receiver 3 outputs a signal according to the intensities of the light beams which are transmitted through the hand 200 and emitted from the palm 200a.

According to the configuration, a gap is hardly formed between the outer circumferential surface of the grasping member 14 which is curved, and the palm 200a of the subject, and the contactness of the light receiver 3 with respect to the palm 200a is enhanced. When the grasping member 14 is grasped by aggressively using the grasp reflex which can be observed in a neonate, particularly, the contactness is further enhanced. Even in the case where the subject of pulse oximetry is a neonate, therefore, it is possible to suppress a measurement error from occurring.

Moreover, the hand 200 of the subject is fixed with respect to the grasping member 14 by the strap 16, and hence a positional displacement between the light emitter 2 and the light receiver 3 due to an unexpected motion of a neonate is prevented from occurring. Even in the case where the subject of pulse oximetry is a neonate, therefore, it is possible to suppress a measurement error from occurring.

The positions of the light emitter 2 and the light receiver 3 may be reversed. Namely, the light emitter 2 may be placed in the grasping member 14, and the light receiver 3 may be placed on the strap 16.

Figure 2C:
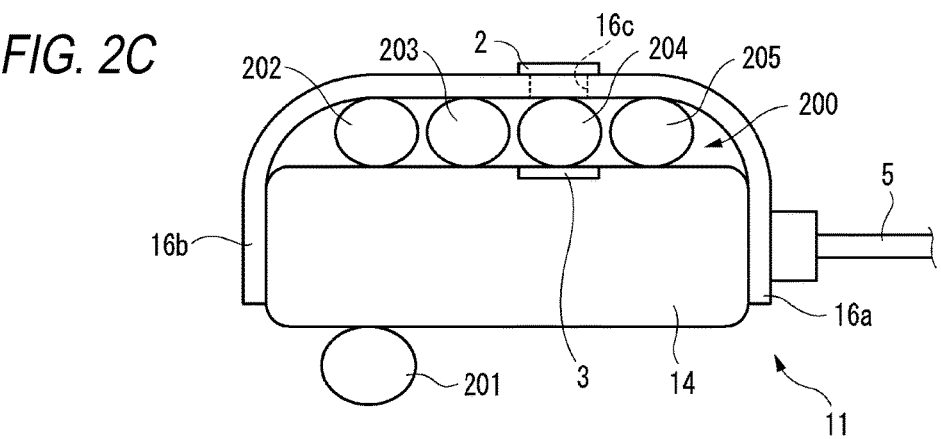

As shown in FIG. 2C, the part of the hand of the subject which is clamped between the strap 16 and the grasping member 14 may be the fingers. The reference numeral 202 denotes a section of the index finger of the subject, 203 denotes a section of the middle finger of the subject, 204 denotes a section of the fourth finger of the subject, and 205 denotes a section of the little finger of the subject. In the example, the light emitter 2 and the light receiver 3 are placed respectively at positions which are opposed to each other across the fourth finger 204 in a state where the fingers 202 to 205 of the subject are clamped between the strap 16 and the grasping member 14.

In the fingers, there is an abundant capillary bed, and hence a change of absorbance of the blood can be easily captured, so that a measurement error can be prevented more surely from occurring. The finger through which the light beams emitted from the light emitter 2 pass is not limited to the fourth finger 204, and alternatively may be either of the index finger 202, the middle finger 203, and the little finger 205.

An adjustment structure which can change the position where the strap 16 is attached to the grasping member 14 in accordance with the size of the part of the hand of the subject may be disposed in the second end portion 16b of the strap 16. Alternatively, the second end portion 16b of the strap 16 may be made undetachable from the grasping member 14, and the strap 16 itself may be made extendable and contractible in accordance with the size of the part of the hand of the subject.

Figure 3:
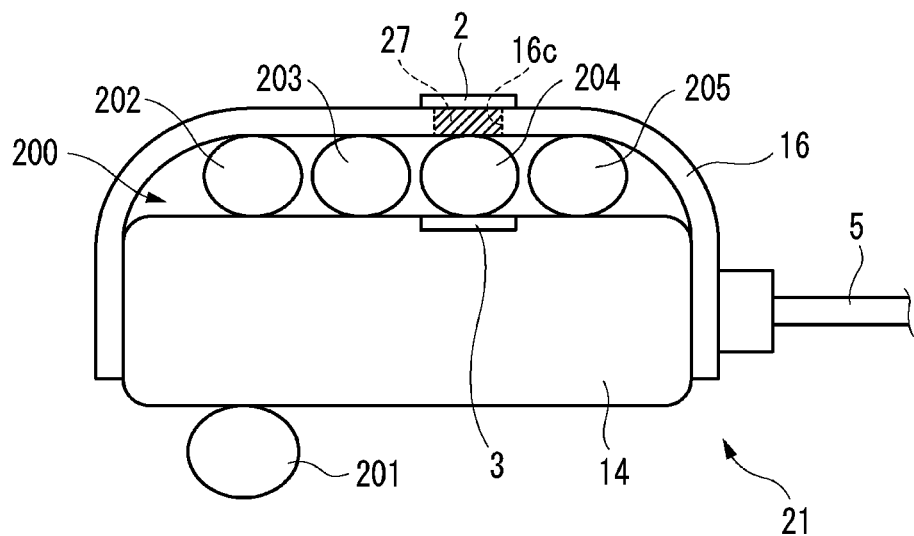
FIG. 3 is a view showing an optical sensor of a third embodiment of the presently disclosed subject matter.

FIG. 3 shows an optical sensor 21 of a third embodiment of the presently disclosed subject matter. The components which are substantially identical to those of the sensor 11 of the second embodiment are denoted by the same reference numerals, and repeated description is omitted. The optical sensor 21 includes the light emitter 2, the light receiver 3, the grasping member 14, the cable 5, the strap 16, and a scattering layer 27.

The scattering layer 27 is fitted into the opening 16c which is formed in the strap 16, and placed in the optical path of the red and infrared light beams emitted from the light emitter 2. The scattering layer 27 may be configured by a resin plate or a non-woven fabric. The red and infrared light beams emitted from the light emitter 2 are scattered while passing through the scattering layer 27, and then enter the fourth finger 204 of the subject.

Since the fingers of the neonate are thin and small, there is a case where at least part of the light beams emitted from the light emitter 2 passes through a gap between the fingers, and the light receiver 3 cannot properly receive the light beams. According to the configuration of the embodiment, a wide light flux which has been scattered by the scattering layer 27 can be caused to surely enter the finger of the subject. Therefore, a measurement error can be prevented more surely from occurring.

The position where the scattering layer 27 is placed is not limited to the interior of the opening 16c of the strap 16. The scattering layer may be placed in an adequate place between the light emitter 2 and a part of the hand of the subject.

The finger through which the light beams emitted from the light emitter 2 pass is not limited to the fourth finger 204, and alternatively may be either of the index finger 202, the middle finger 203, and the little finger 205. Alternatively, the light beams may pass through the palm.

The positions of the light emitter 2 and the light receiver 3 may be reversed. Namely, the light emitter 2 may be placed in the grasping member 14, and the light receiver 3 may be placed on the strap 16. In this case, the scattering layer 27 is placed in the grasping member 14, and at a position through which the red and infrared light beams emitted from the light emitter 2 pass.

Figure 4:
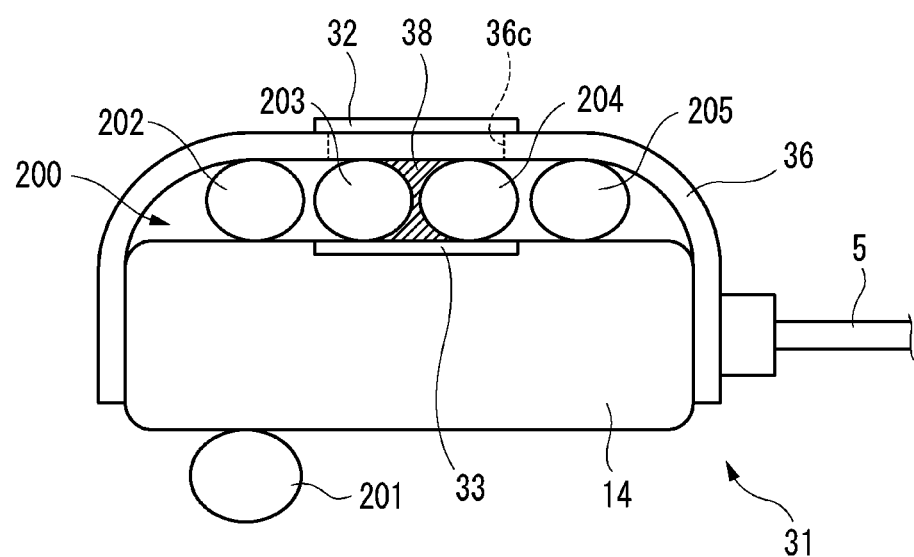
FIG. 4 is a view showing an optical sensor of a fourth embodiment of the presently disclosed subject matter.

FIG. 4 shows an optical sensor 31 of a fourth embodiment of the presently disclosed subject matter. The components which are substantially identical to those of the sensor 11 of the second embodiment are denoted by the same reference numerals, and repeated description is omitted. The optical sensor 31 includes a light emitter 32, a light receiver 33, the grasping member 14, the cable 5, a strap 36, and a light shielding portion 38.

An opening 36c having a size straddling the middle finger 203 and the fourth finger 204 is formed in the strap 36. The light emitter 32 has a light emitting surface having a size through which the red and infrared light beams can be emitted toward the middle finger 203 and the fourth finger 204. The light emitter 32 is placed so that the light emitting surface is opposed to the middle finger 203 and the fourth finger 204 through the opening 36c.

The light receiver 33 has a light receiving surface having a size straddling the middle finger 203 and the fourth finger 204. The light receiving surface of the light receiver 33 is on the outer circumferential surface of the grasping member 14 which is curved, and directed to the outside. The light emitter 32 and the light receiver 33 are placed at positions which are opposed to each other across the middle finger 203 and the fourth finger 204 in a state where the fingers 202 to 205 of the subject are clamped between the strap 36 and the grasping member 14. The light beams emitted from the light emitter 32 pass through the middle finger 203 and the fourth finger 204, and then enter the light receiver 33.

The light shielding portion 38 is formed by a material which does not have transparency. The light shielding portion 38 is placed between places where the middle finger 203 and the fourth finger 204 are located, respectively.

According to the configuration, the light beams emitted from the light emitter 32 surely pass through the fingers of the subject, and then are subjected to the detection by the light receiver 33. Since the light shielding portion 38 is placed in the gap between the fingers, moreover, it is possible to eliminate an influence which may be exerted by light passing through the gap, on the detection by the light receiver 33. Even in the case where the subject of pulse oximetry is a neonate having the fingers which are thin and small, therefore, it is possible to suppress a measurement error from occurring.

In the configuration shown in FIG. 4, the light shielding portion 38 may be placed also in at least one of places between the positions where the index finger 202 and the middle finger 203 are located, and between the positions where the fourth finger 204 and the little finger 205 are located.

The fingers through which the light beams emitted from the light emitter 32 pass are not limited to the middle finger 203 and the fourth finger 204. A configuration may be employed where the light beams pass through two or more fingers selected from the fingers 202 to 205. For example, the light beams may pass through the index finger 202 and the middle finger 203. In this case, the light shielding portion 38 is placed between the positions where the index finger 202 and the middle finger 203 are located.

A scattering layer may be disposed between the light emitter 32 and the fingers 202 to 205. In this case, the light beams emitted from the light emitter 32 can enter easily and surely also three or more fingers.

The positions of the light emitter 32 and the light receiver 33 may be reversed. Namely, the light emitter 32 may be placed in the grasping member 14, and the light receiver 33 may be placed on the strap 36.

Figure 5A:
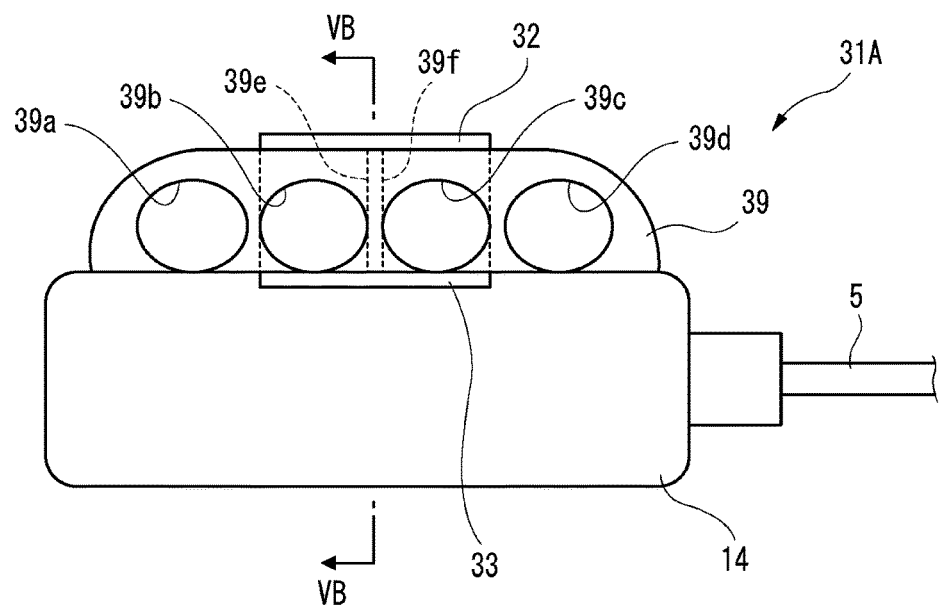
FIGS. 5A and 5B are views showing an optical sensor of a modification of the fourth embodiment.
Figure 5B:
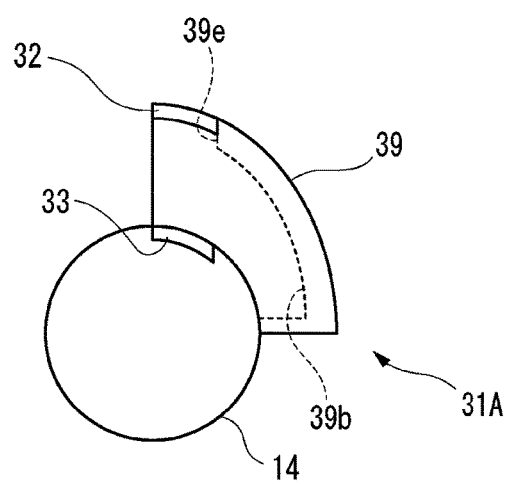

FIG. 5A shows an optical sensor 31A of a modification of the fourth embodiment. The components which are substantially identical to those of the sensor 31 of the fourth embodiment are denoted by the same reference numerals, and repeated description is omitted. FIG. 5B is a sectional view taken along line VB-VB in FIG. 5A. The optical sensor 31 includes the light emitter 32, the light receiver 33, the grasping member 14, the cable 5, and a finger holder 39.

The finger holder 39 (an example of the clamping member) is formed integrally with a part of the outer circumferential surface of the grasping member 14. A hole 39a, a hole 39b, a hole 39c, and a hole 39d are formed in the finger holder 39. In a state where the hand of the subject grasps the grasping member 14, the index finger, the middle finger, the fourth finger, and the little finger are inserted into the hole 39a, the hole 39b, the hole 39c, and the hole 39d, respectively. Namely, the fingers 202 to 205 which are a part of the hand of the subject are clamped between the finger holder 39 and the grasping member 14.

The finger holder 39 is formed by a material having a light shielding property. A through hole 39e which communicates with the hole 39b, and a through hole 39f which communicates with the hole 39c are formed in a part of the finger holder 39. The light emitting surface of the light emitter 32, and the light receiving surface of the light receiver 33 are placed so as to be opposed to each other through the through holes 39e, 39f. In a state where the hand of the subject grasps the grasping member 14, the light beams emitted from the light emitter 32 pass through the through holes 39e, 39f to enter the middle finger and fourth finger of the subject. The light beams which have passed through the middle finger and the fourth finger are subjected to the detection by the light receiver 33.

Also according to the configuration, the light beams emitted from the light emitter 32 surely pass through the fingers of the subject, and then are subjected to the detection by the light receiver 33. The portion other than the through holes 39e, 39f in the finger holder 39 which is formed integrally with the grasping member 14 is formed by the material having a light shielding property. Therefore, only light beams passing through the fingers are subjected to the detection by the light receiver 33. Even in the case where the subject is a neonate having the fingers which are thin and small, therefore, it is possible to suppress a measurement error from occurring.

The positions where the through holes 39e, 39f are formed are not limited to those communicating with the holes 39b, 39c. Alternatively, two or more through holes may be formed so as to communicate with two or more holes selected from the holes 39a to 39d.

A scattering layer may be disposed between the light emitter 32 and the holes 39a to 39d. In this case, the light beams emitted from the light emitter 32 can enter easily and surely also three or more fingers.

The positions of the light emitter 32 and the light receiver 33 may be reversed. Namely, the light emitter 32 may be placed in the grasping member 14, and the light receiver 33 may be placed in the finger holder 39.

When a pressure produced by grasping is locally concentrated to the tissue of the subject, the blood flow in the tissue is constricted, and the correctness of detection of the received light intensity by the light receiver 33 is lowered. All the grasping members 4, 14 in the embodiments shown in FIGS. 1A to 5B have a shape of a rotating body which is symmetric about the axis extending in the longitudinal direction. According to the configuration, it is possible to relax local stress concentration which is applied to the tissue of the subject, and it is further possible to ensure high contactness between the hand of the subject and the grasping member, in a wide range. Even in the case where the subject of pulse oximetry is a neonate, therefore, it is possible to suppress a measurement error from occurring.

Figure 6A:
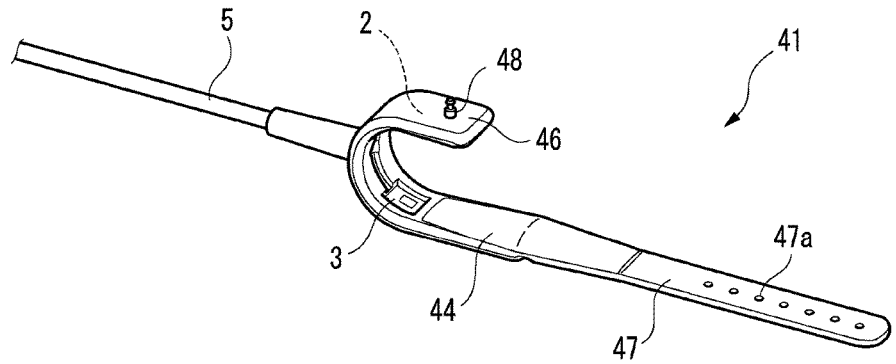
FIGS. 6A to 6C are views showing an optical sensor of a fifth embodiment of the presently disclosed subject matter.
Figure 6B:
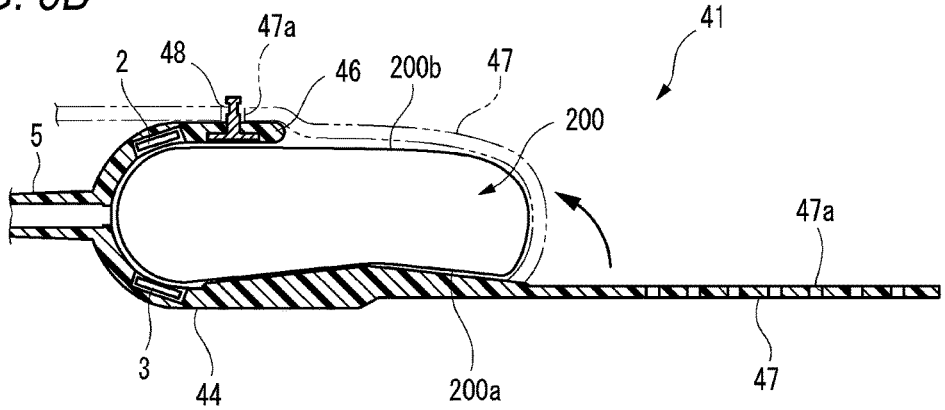

FIG. 6A shows an optical sensor 41 of a fifth embodiment of the presently disclosed subject matter, and FIG. 6B is a longitudinal sectional view showing the configuration of the optical sensor 41. The components which are substantially identical to those of the sensor 1 of the first embodiment are denoted by the same reference numerals, and repeated description is omitted. The optical sensor 41 includes the light emitter 2, the light receiver 3, a grasping member 44, a clamping member 46, a belt member 47, a hook 48, and the cable 5.

The grasping member 44 has a rod-like shape which is to be grasped by the subject. The light receiver 3 is disposed in the grasping member 44. In the outer circumferential surface of the grasping member 44 which is curved, the light receiving surface of the light receiver 3 is directed toward the clamping member 46.

The clamping member 46 extends in the longitudinal direction of the grasping member 44. The light emitter 2 is disposed in the clamping member 46. The light emitting surface of the light emitter 2 is directed toward the grasping member 44.

The grasping member 44 and the clamping member 46 have a degree of rigidity by which the positional relationship between the light emitter 2 and the light receiver 3 is made constant. The grasping member 44 and the clamping member 46 forma space for clamping the hand of the subject, therebetween. In FIG. 6B, 200 denotes a section of the hand of the subject, 200a denotes the palm of the subject, and 200b denotes the back of the hand of the subject.

One end of the belt member 47 is fixed to the grasping member 44. The belt member 47 extends in the longitudinal direction of the grasping member 44. A plurality of holes 47a are arranged in the longitudinal direction. As indicated by the dash-dot-dot lines in FIG. 6B, the belt member 47 is wound around the back 200b of the hand, and the hook 48 is fitted into one (an example of the belt member) of the holes 47a, whereby the belt member 47 is fixed to the clamping member 46, and the optical sensor 41 is fixed to the hand 200. In this state, the light emitter 2 and the light receiver 3 are placed respectively at positions opposed to each other across the hand 200. The hook 48 is engageable with and disengageable from the holes 47a, and therefore the belt member 47 is attachable to and detachable from the clamping member 46.

According to the configuration, the work of passing the hand of the subject between the grasping member and the clamping member as in the above-described embodiments is not necessary. The fixation of the optical sensor 41 is completed simply by causing the subject to grasp the opened grasping member 44, and, in this state, winding the belt member 47 around the hand 200 of the subject. Sure attachment is enabled, and hence, even in the case where the subject of pulse oximetry is a neonate having the fingers which are thin and small, it is possible to suppress a measurement error from occurring.

Since the plurality of holes 47a are formed in the belt member 47, the hook 48 can be fitted into one of the holes 47a which is at the optimum position, in accordance with the size of the hand 200 of the subject. Namely, a part of the belt member 47 which is fixed to the clamping member 46 in an attachable and detachable manner is variable.

According to the configuration, it is possible to ensure a sure attachment state according to the size of the hand which is different depending on the subject. Even in the case where the subject of pulse oximetry is a neonate having the small hands, therefore, it is possible to suppress a measurement error from occurring.

The positions of the light emitter 2 and the light receiver 3 may be reversed. Namely, the light emitter 2 may be placed in the grasping member 44, and the light receiver 3 may be placed on the clamping member 46.

A configuration where one end of the belt member 47 is fixed to the clamping member 46, and the hook 48 is disposed on the grasping member 44 may be employed. In this case, a part of the belt member 47 is fixed to the grasping member 44 in an attachable and detachable manner.

Figure 6C:
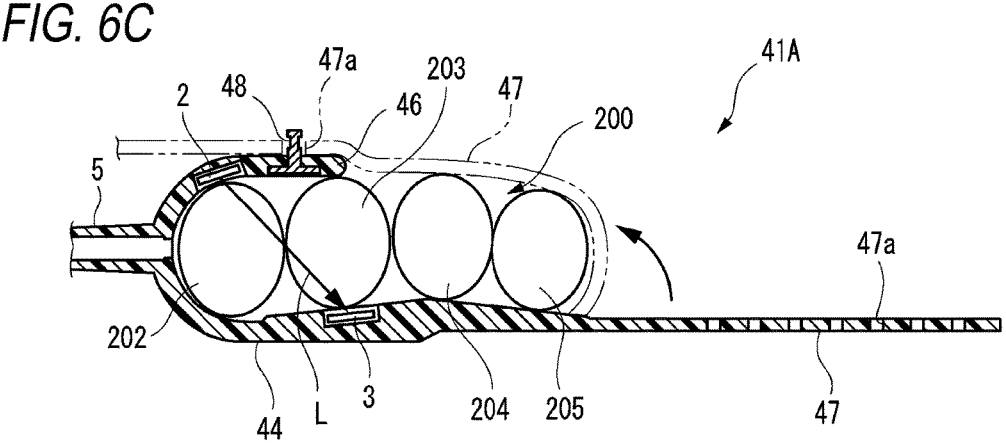

As in an optical sensor 41A of a modification of the fifth embodiment shown in FIG. 6C, the light emitter 2 and the light receiver 3 may be placed so that light L emitted from the light emitter 2 passes through a plurality of fingers (in this example, the index finger 202 and the middle finger 203), and then reaches the light receiver 3.

According to the configuration, the light emitted from the light emitter 2 surely passes through the fingers of the subject, and then is subjected to the detection by the light receiver 3. Even in the case where the subject of pulse oximetry is a neonate having the fingers which are thin and small, therefore, it is possible to suppress a measurement error from occurring.

Figure 7:
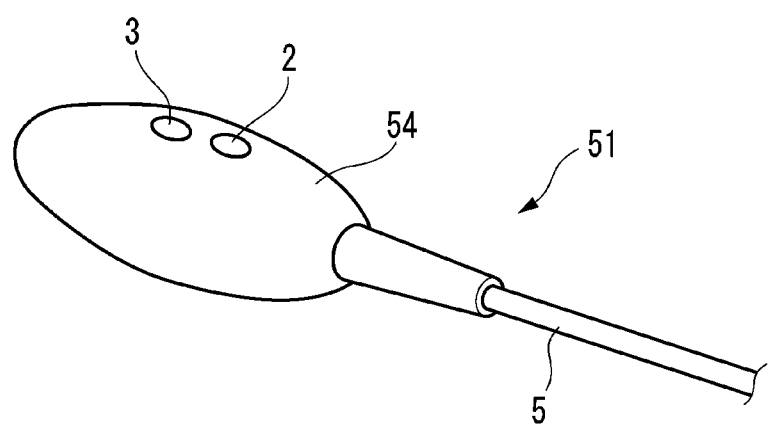
FIG. 7 is a view showing an optical sensor of a sixth embodiment of the presently disclosed subject matter.

FIG. 7 shows an optical sensor 51 of a sixth embodiment of the presently disclosed subject matter. The components which are substantially identical to those of the sensor 1 of the first embodiment are denoted by the same reference numerals, and repeated description is omitted. The optical sensor 51 includes the light emitter 2, the light receiver 3, a grasping member 54, and the cable 5.

In the grasping member 4 of the optical sensor 1 of the first embodiment, the diameter is constant along the axis extending in the longitudinal direction. By contrast, the grasping member 54 in the present embodiment is different in that the diameter is changed along the axis extending in the longitudinal direction. The grasping member 54 has a shape of a rotating ellipsoidal body in which the diameter is increased as advancing from end portions in the longitudinal direction toward a middle portion.

According to the configuration, the outer circumferential surface of the grasping member 54 is curved also in the longitudinal direction, and hence the contactness with the hand of the subject is further improved. Even in the case where the subject is a neonate, therefore, it is possible to suppress a measurement error from occurring.

At least the optical sensor 1, 31A, 41, 51 among the optical sensors 1, 11, 21, 31, 31A, 41, 51 which have been described above, the positional relationship between the light emitter 2 and the light receiver 3 is constant.

According to the configuration, even when the hand of the subject moves or the grasping force is changed, the positional relationship with respect to the skin is hardly changed, and hence the light emitted from the light emitter is surely received by the light receiver, and noises are prevented from being produced. Even in the case where the subject of pulse oximetry is a neonate whose motion is unpredictable, therefore, it is possible to suppress a measurement error from occurring.

A configuration where at least a part is flexible in the grasping members 4, 14, 44, 54 in the above embodiments may be employed. For example, the surfaces of the grasping members 4, 14, 44, 54 are formed by a material which is deformable by a pressure from the skin of the subject or a grasping force, such as silicone rubber or a sponge, or a hollow structure such as a rubber ball is employed, whereby the contactness with the outer circumferential surface of the grasping member 4, 14, 44, or 54 can be enhanced irrespective of the size of the hand of the subject. Even in the case where the subject is a neonate, therefore, it is possible to suppress a measurement error from occurring.

Figure 8A:
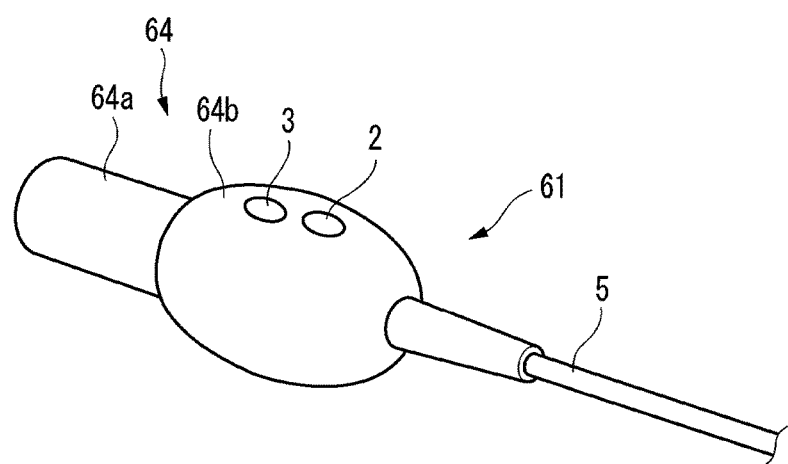
FIGS. 8A and 8B are views showing an optical sensor of a seventh embodiment of the presently disclosed subject matter.

FIG. 8A shows an optical sensor 61 of a seventh embodiment of the presently disclosed subject matter. The components which are substantially identical to those of the sensor 1 of the first embodiment are denoted by the same reference numerals, and repeated description is omitted. The optical sensor 61 includes the light emitter 2, the light receiver 3, a grasping member 64, and the cable 5.

Figure 8B:
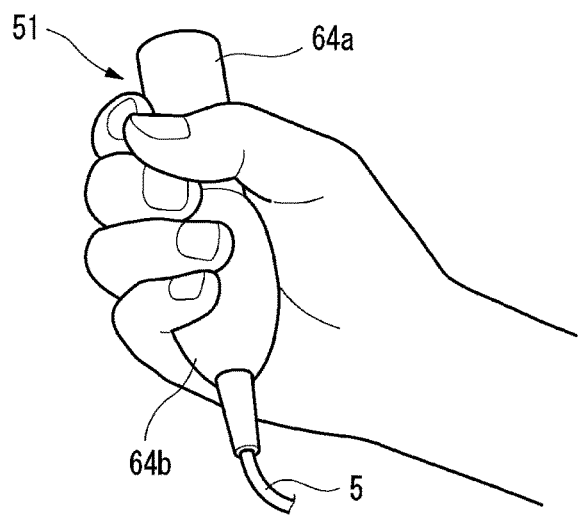

The grasping member 64 has a first portion 64a and a second portion 64b. FIG. 8B shows a state in which the grasping member 64 is grasped by the subject. In this state, the first portion 64a is opposed to at least the thumb and index finger of the subject, and the second portion 64b is opposed to the palm of the subject. The light emitter 2 and the light receiver 3 are disposed in the second portion 64b.

The first portion 64a is higher in rigidity than the second portion 64b, and the second portion 64b is higher in flexibility than the first portion 64a. For example, at least the surface of the first portion 64a may be formed by a material such as hard plastic, and at least the surface of the second portion 64b may be formed by a material such as silicone rubber or a sponge.

In grasping, the thumb and the index finger tend to easily exert a force. According to the configuration, the grasping force exerted by the subject is received by the first portion 64a having a relatively high rigidity. Therefore, the attitude of the grasping member 64 is stabilized, and the accuracy of detection of the received light intensity can be prevented from being lowered by stress concentration in the second portion 64b where the light emitter 2 and the light receiver 3 are disposed. By contrast, the second portion 64b has a relatively high flexibility, and hence the contactness with the hand of the subject can be enhanced. By aggressively using the grasp reflex which can be observed in, particularly, a neonate, therefore, it is possible to suppress a measurement error in pulse oximetry from occurring.

In the embodiment, the shapes of the first portion 64a and the second portion 64b are different from each other. In the first portion 64a, the diameter is constant along the axis extending in the longitudinal direction. By contrast, the second portion 64b has a shape of a rotating ellipsoidal body in which the diameter is increased as advancing from end portions in the longitudinal direction toward a middle portion. According to the configuration, the first portion 64a can be stably grasped by the thumb and index finger of the subject, and the contactness between the second portion 64b and the hand of the subject is improved.

However, it is not always required that the shapes of the first portion 64a and the second portion 64b are different from each other. The both portions may have the same shape as far as the rigidity of the first portion 64a is higher than that of the second portion 64b, and the flexibility of the second portion 64b is higher than that of the first portion 64a. In this case, the shape of the whole grasping member is similar to the shapes of the grasping members 4, 14, 44, 54 which have been described in the above embodiments.

Moreover, it is not always required that the first portion 64a which is higher in rigidity than the second portion 64b is disposed in only the portion where the thumb and index finger of the subject are to be placed. A further first portion 64a may be disposed on the side where the cable 5 is disposed, as far as the second portion 64b in which the light emitter 2 and the light receiver 3 are placed has a higher flexibility.

Figure 9:
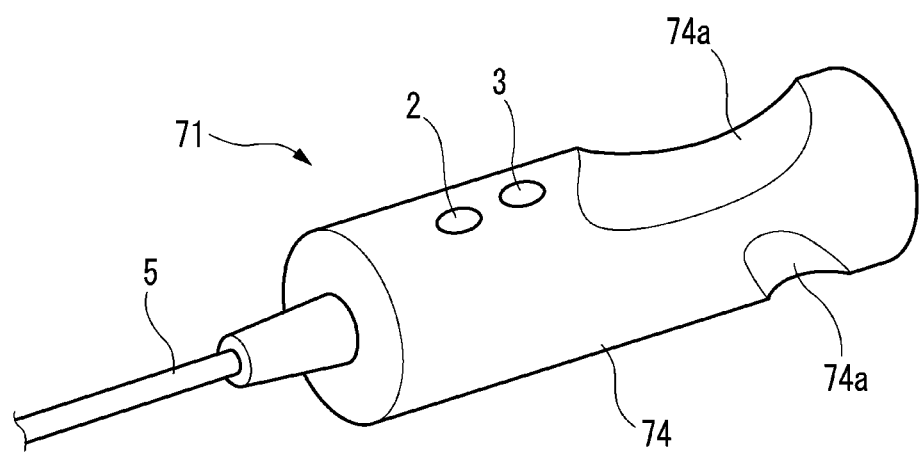
FIG. 9 is a view showing an optical sensor of an eighth embodiment of the presently disclosed subject matter.

FIG. 9 shows an optical sensor 71 of an eighth embodiment of the presently disclosed subject matter. The components which are substantially identical to those of the sensor 1 of the first embodiment are denoted by the same reference numerals, and repeated description is omitted. The optical sensor 71 includes the light emitter 2, the light receiver 3, a grasping member 74, and the cable 5.

A groove 74a (an example of the recess) is formed in the outer circumferential surface of the grasping member 74.

The groove 74a is defined to have a shape to which, in grasping, the fingers of the right hand of the subject are fitted. Namely, the grasping member 74 has a whole shape which is asymmetric about the axis extending in the longitudinal direction.

In congenital heart disease screening in neonates, it is necessary to measure the arterial oxygen saturation in the right hand of the subject. When the measurement is erroneously performed on the left hand, there is a case where a correct screening result cannot be obtained. According to the above-described configuration, when the grasping member 74 is disposed to be grasped by the left hand of the subject, the fingers of the left hand fail to be fitted to the groove 74a, and hence the medical person can be aware of the error before measurement. In congenital heart disease screening in neonates, therefore, it is possible to suppress a measurement error from occurring in pulse oximetry.

The shape of the groove 74a which is formed in the outer circumferential surface of the grasping member 74 is not limited to that to which the fingers of the right hand of the subject are fitted. A recess having an adequate shape may be formed as far as it can accommodate a part of the right hand of the subject.

Figure 10:
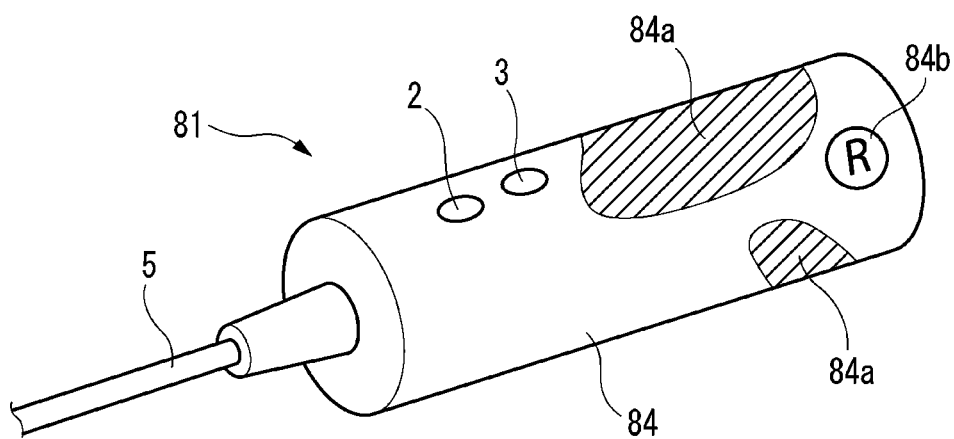
FIG. 10 is a view showing an optical sensor of a ninth embodiment of the presently disclosed subject matter.

FIG. 10 shows an optical sensor 81 of a ninth embodiment of the presently disclosed subject matter. The components which are substantially identical to those of the sensor 1 of the first embodiment are denoted by the same reference numerals, and repeated description is omitted. The optical sensor 81 includes the light emitter 2, the light receiver 3, a grasping member 84, and the cable 5.

The grasping member 84 includes a first guiding indicator 84a and a second guiding indicator 84b on the outer circumferential surface. The first guiding indicator 84a has an outline having a shape corresponding to the fingers of the right hand of the subject, and presents a color which is different from that of the other portion. The second guiding indicator 84b includes a character indicating "right". Namely, the first guiding indicator 84a and the second guiding indicator 84b guide grasping by the right hand of the subject.

Also according to the configuration, in congenital heart disease screening in neonates, grasping by the right hand of the subject can be strongly indicated to the medical person, and it is possible to suppress a measurement error from occurring in pulse oximetry. The whole shape itself of the grasping member 84 is symmetrical about the axis extending in the longitudinal direction. Therefore, the cost of processing components can be suppressed as compared to a configuration such as that of the grasping member 74 of the optical sensor 71 of the eighth embodiment.

When grasping by the right hand of the subject can be guided, at least one of the first guiding indicator 84a and the second guiding indicator 84b may be disposed.

Figure 11:
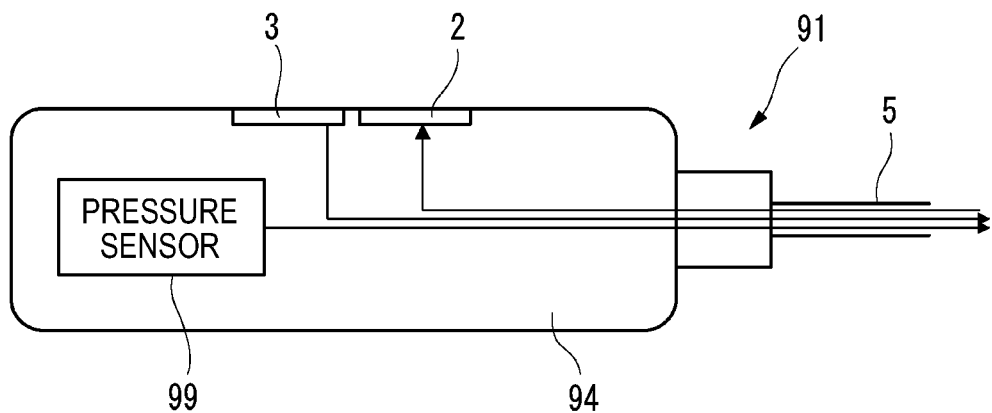
FIG. 11 is a view showing an optical sensor of a tenth embodiment of the presently disclosed subject matter.

FIG. 11 shows an optical sensor 91 of a tenth embodiment of the presently disclosed subject matter. The components which are substantially identical to those of the sensor 1 of the first embodiment are denoted by the same reference numerals, and repeated description is omitted. The optical sensor 91 includes the light emitter 2, the light receiver 3, a grasping member 94, the cable 5, and a pressure sensor 99.

The pressure sensor 99 is disposed in the grasping member 94. The pressure sensor 99 may directly detect the grasping pressure exerted by the subject, or indirectly detect the grasping pressure by detecting distortion or deformation of the grasping member 94. In the case where the grasping member 94 is configured as a hollow structure such as a rubber ball, the grasping pressure may be indirectly detected by detecting a change of the air pressure of the hollow structure due to deformation. Namely, the pressure sensor 99 detects a state change of at least a part of the grasping member 94 due to the grasping pressure exerted by the subject. The pressure sensor 99 outputs a signal corresponding to the state change to the measuring apparatus which is not shown, via the cable 5.

As described above, the pressure which is produced by grasping causes the blood volume in the tissue of the subject to be reduced, thereby changing the intensity of light received by the light receiver 3. This change appears as noises in measurement of the arterial oxygen saturation. A change of the grasping pressure correlates with that of the intensity of received light. When components relating to the correlation are removed away from the output signal of the light receiver 3 based on the output of the pressure sensor 99, therefore, the measurement accuracy is improved. Also in the case where the subject of pulse oximetry is a neonate in which a change of the grasping pressure is unpredictable, therefore, it is possible to suppress a measurement error from occurring.

When the output signal of the pressure sensor 99 is monitored, moreover, it is possible to quantitatively evaluate a reaction or the grasp reflex of a neonate who is the subject. In the case where the grasp reflex is very weak or cannot be observed, for example, there is suspicion of serious brain injury or upper spinal cord lesion. Namely, screening for an abnormality of the cerebral nervous system can be performed in conjunction with congenital heart disease screening by monitoring of the arterial oxygen saturation.

The pressure sensor 99 may be disposed in any one of the grasping members 4, 14, 44, 54, 64, 74, 84 in the above embodiments.

Figure 12:
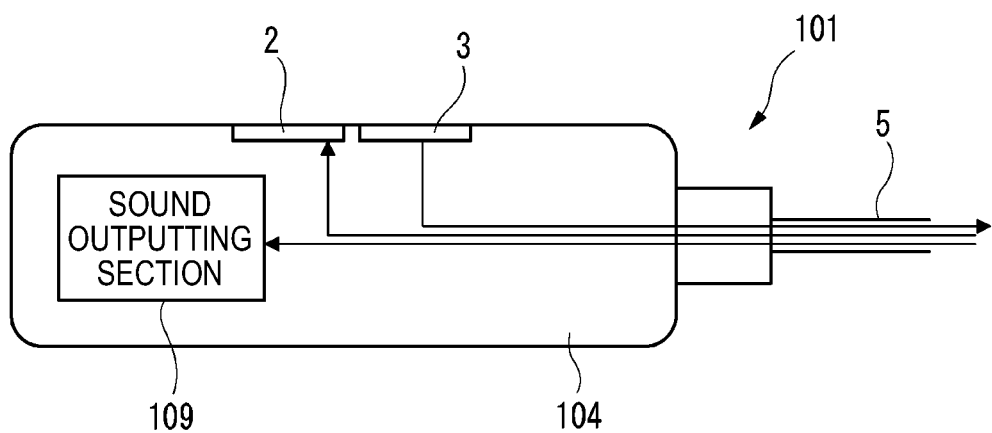
FIG. 12 is a view showing an optical sensor of an eleventh embodiment of the presently disclosed subject matter.

FIG. 12 shows an optical sensor 101 of an eleventh embodiment of the presently disclosed subject matter. The components which are substantially identical to those of the sensor 1 of the first embodiment are denoted by the same reference numerals, and repeated description is omitted. The optical sensor 101 includes the light emitter 2, the light receiver 3, a grasping member 104, the cable 5, and a sound outputting section 109.

The sound outputting section 109 is disposed in the grasping member 104. The sound outputting section 109 outputs predetermined sound in accordance with a control signal which is input from a controller (not shown) via the cable 5. Preferably, the predetermined sound is sound which suppresses excitement of a neonate who is the subject. Examples of such sound are comfortable and relaxing sound such as water flowing sound, womb sound, and voice of the mother. Alternatively, sound which attracts the interest of a neonate who is the subject is preferably used. When the output pattern of sound is periodically changed, for example, the interest of a neonate is attracted, and a body motion can be suppressed.

According to the configuration, a body motion of the subject who is a neonate can be suppressed, and the contactness between the grasping member 104 and the hand can be maintained. Also in the case where the subject of pulse oximetry is a neonate, therefore, it is possible to suppress a measurement error from occurring.

The sound outputting section 109 may be disposed in any one of the grasping members 4, 14, 44, 54, 64, 74, 84, 94 in the above embodiments. In the case where the sound outputting section 109 is disposed in the grasping member 94 of the optical sensor 91 of the tenth embodiment, a configuration where predetermined sound is output in accordance with detection of the grasping pressure by the pressure sensor 99 may be employed.

The sound outputting section 109 is not always required to be disposed in any one of the grasping members in the above embodiments. Alternatively, the sound outputting section 109 may be disposed on the side of the external apparatus to which the optical sensor of each of the above embodiments is connected. In the alternative, wirings which are necessary in the sound outputting section 109 can be omitted from the cable 5, and hence the cable 5 becomes more flexible. Also in the case where the subject of pulse oximetry is a neonate, therefore, it is possible to suppress a measurement error from occurring.

Figure 13:
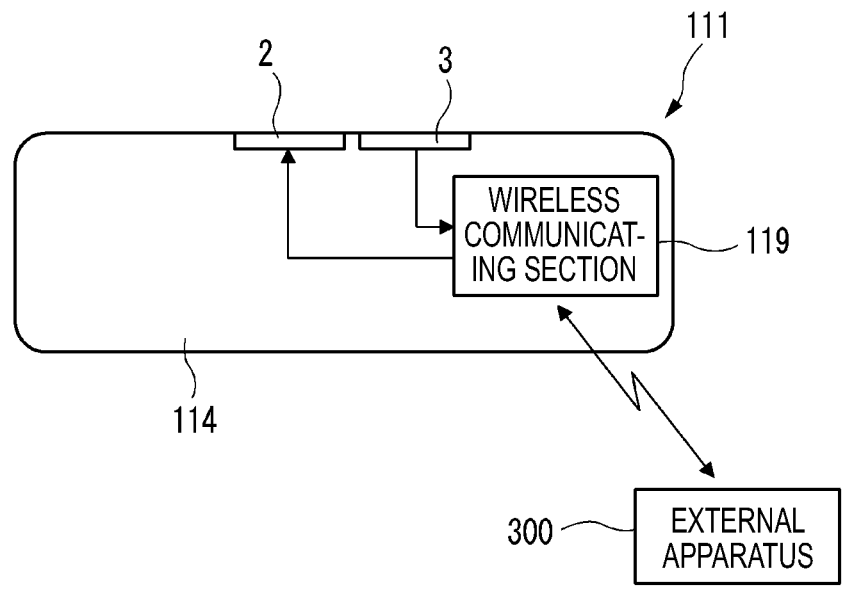
FIG. 13 is a view showing an optical sensor of a twelfth embodiment of the presently disclosed subject matter.

FIG. 13 shows an optical sensor 111 of a twelfth embodiment of the presently disclosed subject matter. The components which are substantially identical to those of the sensor 1 of the first embodiment are denoted by the same reference numerals, and repeated description is omitted. The optical sensor 111 includes the light emitter 2, the light receiver 3, a grasping member 114, the cable 5, and a wireless communicating section 119.

The wireless communicating section 119 transmits and receives a signal between the light emitter 2 and the light receiver 3, and an external apparatus 300. For example, the wireless communicating section 119 receives a light emission control signal from the external apparatus 300, and causes the light emitter 2 to emit light. Moreover, for example, the wireless communicating section 119 transmits a signal which is output from the light receiver 3, and which corresponds to the intensity of the light, to the external apparatus 300. The external apparatus 300 performs an output (display, printing, or the like) of biological information corresponding to the signal.

According to the configuration, a cable which connects the optical sensor 111 to the external apparatus 300 can be omitted. It is possible to avoid a situation such as that a cable is tangled with the subject by an unexpected motion. Also in the case where the subject of pulse oximetry is a neonate, therefore, it is possible to suppress a measurement error from occurring.

Figure 14:
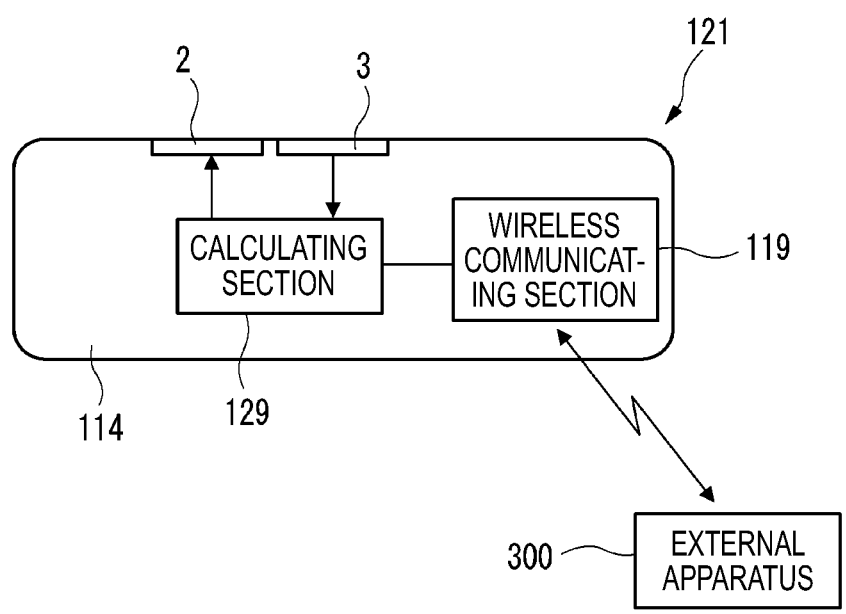
FIG. 14 is a view showing an optical sensor of a thirteenth embodiment of the presently disclosed subject matter.

FIG. 14 shows an optical sensor 121 of a thirteenth embodiment of the presently disclosed subject matter. The components which are substantially identical to those of the sensor 111 of the twelfth embodiment are denoted by the same reference numerals, and repeated description is omitted. The optical sensor 121 includes a calculating section 129 in addition to the light emitter 2, the light receiver 3, the grasping member 114, the cable 5, and the wireless communicating section 119.

The calculating section 129 performs a calculation process on a signal communicated between the light emitter 2 and the light receiver 3, and the wireless communicating section 119. For example, the calculating section 129 performs at least a part of calculation processes to be executed by the external apparatus 300.

Also according to the configuration, a cable which connects the optical sensor 121 to the external apparatus 300 can be omitted. It is possible to avoid a situation such as that a cable is tangled with the subject by an unexpected motion. Also in the case where the subject of pulse oximetry is a neonate, therefore, it is possible to suppress a measurement error from occurring.

In the above-described embodiments, the light emitter 2 and the light receiver 3 are supported by a member having a light shielding property. Here, the terms "member having a light shielding property" means not only a member which has no transparency, but also a member which has a certain degree of transparency and also a light shielding property, such as a translucent member.

According to the configuration, light other than that emitted from the light emitter 2 can be prevented from entering the light receiver 3 from the outside. Also in the case where the subject of pulse oximetry is a neonate, therefore, it is possible to suppress a measurement error from occurring.

The embodiments have been described in order to facilitate understanding of the invention, and are not intended to limit the invention. It is a matter of course that the invention may be changed or improved without departing the spirit thereof, and includes equivalent of the embodiments.

The above embodiments have been described under the assumption that pulse oximetry is performed while setting a neonate as the subject. However, the subject is not limited to a neonate. When the size of the optical sensor is adequately set, an adult may be set as the subject. The optical sensor of the presently disclosed subject matter may be used in acquisition of adequate biological information in which a light emitter and a light receiver are used. The values and number of the frequencies of light emitted from the light emitter may be properly determined according to the use purpose.

According to the presently disclosed subject matter, there may be provided an optical sensor comprising: a light emitter; a light receiver; and a rod-shaped grasping member in which the light emitter and the light receiver are disposed, and which is to be grasped by a hand of a subject.

According to the above configuration, a gap is hardly formed between the grasping member and the hand of the subject, and the contactness of the light emitter and the light receiver with the hand is enhanced. When the grasping member is grasped by aggressively using the grasp reflex which can be observed in, particularly, a neonate, the contactness is further enhanced. Even in the case where the subject of pulse oximetry is a neonate, therefore, it is possible to suppress a measurement error from occurring.

According to the presently disclosed subject matter, there may be provided an optical sensor comprising: a light emitter; a light receiver; a rod-shaped grasping member in which one of the light emitter and the light receiver is disposed, and which is to be grasped by a hand of a subject; and a clamping member which is adapted to clamp a part of the hand of the subject with the grasping member, another one of the light emitter and the light receiver being disposed in the clamping member.

According to the above configuration, a gap is hardly formed between the grasping member and the part of the hand of the subject, and the contactness of the light receiver with the part of the hand is enhanced. When the grasping member is grasped by aggressively using the grasp reflex which can be observed in, particularly, a neonate, the contactness is further enhanced. Even in the case where the subject of pulse oximetry is a neonate, therefore, it is possible to suppress a measurement error from occurring.

Moreover, the part of the hand of the subject is fixed with respect to the grasping member by the clamping member, and hence a positional displacement between the light emitter and the light receiver due to an unexpected motion of a neonate is prevented from occurring. Even in the case where the subject of pulse oximetry is a neonate, therefore, it is possible to suppress a measurement error from occurring.

The optical sensor may further comprise: a scattering layer which is placed in an optical path of light emitted from the light emitter.

Since the fingers of a neonate are thin and small, there is a case where at least part of the light emitted from the light emitter passes through a gap between the fingers, and the light receiver cannot properly receive the light. According to the above configuration, a wide light flux which has been scattered by the scattering layer can be caused to surely enter the finger of the subject. Therefore, a measurement error can be prevented more surely from occurring.

The light emitter may be placed so that emitted light passes through a plurality of fingers of the subject.

According to the above configuration, the light emitted from the light emitter surely passes through the fingers of the subject, and then is subjected to the detection by the light receiver. Even in the case where the subject of pulse oximetry is a neonate having the fingers which are thin and small, therefore, it is possible to suppress a measurement error from occurring.

The optical sensor may further comprise: a light shielding member which is disposed between the plurality of fingers.

According to the above configuration, it is possible to eliminate an influence which may be exerted by light passing between the fingers, on the detection by the light receiver. Even in the case where the subject of pulse oximetry is a neonate having the fingers which are thin and small, therefore, it is possible to suppress a measurement error from occurring.

The optical sensor may further comprise: a belt member, one end of the belt member may be fixed to one of the grasping member and the clamping member, and a part of the belt member may be attachable to and detachable from the other of the grasping member and the clamping member.

According to the above configuration, the work of passing the hand of the subject between the grasping member and the clamping member is not necessary. Fixation of the optical sensor is completed simply by causing the subject to grasp the opened grasping member, and, in this state, winding the belt member around the hand of the subject. Sure attachment is enabled, and hence, even in the case where the subject of pulse oximetry is a neonate, it is possible to suppress a measurement error from occurring.

The part of the belt member may be variable.

According to the above configuration, it is possible to ensure a sure attachment state according to the size of the hand which is different depending on the subject. Even in the case where the subject of pulse oximetry is a neonate, therefore, it is possible to suppress a measurement error from occurring.

The grasping member may have a shape of a rotating body.

According to the above configuration, the grasping member has a shape which is symmetric about the axis extending in one direction. Therefore, it is possible to relax local stress concentration which is due to grasping, and which is applied to the tissue of the subject, and it is further possible to ensure high contactness between the hand of the subject and the grasping member, in a wide range. Even in the case where the subject of pulse oximetry is a neonate, therefore, it is possible to suppress a measurement error from occurring.

A positional relationship between the light emitter and the light receiver may be constant.

According to the above configuration, even when the hand of the subject moves or the grasping force is changed, the light emitted from the light emitter is surely received by the light receiver. Even in the case where the subject of pulse oximetry is a neonate whose motion is unpredictable, therefore, it is possible to suppress a measurement error from occurring.

At least a part of the grasping member may be flexible.

According to the above configuration, the contactness with the grasping member can be enhanced irrespective of the size of the hand of the subject. Even in the case where the subject of pulse oximetry is a neonate, therefore, it is possible to suppress a measurement error from occurring.

The grasping member may include a first portion in which at least a thumb and index finger of the subject are to be placed, and a second portion in which at least one of the light emitter and the light receiver is disposed, the first portion may be higher in rigidity than the second portion, and the second portion may be higher in flexibility than the first portion.

In grasping, the thumb and the index finger tend to easily exert a force. According to the above configuration, the first portion having a relatively high rigidity receives the grasping force exerted by the subject. Therefore, the attitude of the grasping member is stabilized, and the accuracy of detection of the received light intensity can be prevented from being lowered by stress concentration in the second portion where the light emitter and the light receiver are disposed. By contrast, the second portion has a relatively high flexibility, and hence the contactness with the hand of the subject can be enhanced. By aggressively using the grasp reflex which can be observed in, particularly, a neonate, therefore, it is possible to suppress a measurement error in pulse oximetry from occurring.

An outer circumferential surface of the grasping member may include a recess having a shape which is adapted to receive a part of a right hand of the subject.

In congenital heart disease screening in neonates, it is necessary to measure the arterial oxygen saturation in the right hand of the subject. When the measurement is erroneously performed on the left hand, there is a case where a correct screening result cannot be obtained. According to the above configuration, even when the grasping member is disposed to be grasped by the left hand of the subject, the fingers of the left hand fail to be fitted to the recess, and hence the medical person can be aware of the error before measurement. In congenital heart disease screening in neonates, therefore, it is possible to suppress a measurement error from occurring in pulse oximetry.

The optical sensor may further comprise: an indicator guiding grasping by the right hand of the subject.

Also according to the above configuration, in congenital heart disease screening in neonates, grasping by the right hand of the subject can be strongly indicated to the medical person, and it is possible to suppress a measurement error from occurring in pulse oximetry. Moreover, it is not required to form a recess in the grasping member, and hence the cost of processing components can be suppressed.

The optical sensor may further comprise: a sensor which is configured to detect a state change of at least a part of the grasping member, the change being due to a grasping pressure exerted by the subject.

A pressure which is produced by grasping causes the blood volume in the tissue of the subject to be reduced, thereby changing the intensity of light received by the light receiver. This change appears as noises in measurement of the arterial oxygen saturation. A change of the grasping pressure correlates with that of the intensity of received light. When components relating to the correlation are removed away from an output signal of the light receiver based on the output of the sensor, therefore, the measurement accuracy is improved. Also in the case where the subject of pulse oximetry is a neonate in which a change of the grasping pressure is unpredictable, therefore, it is possible to suppress a measurement error from occurring.

When the output signal of the sensor is monitored, moreover, it is possible to quantitatively evaluate a reaction or the grasp reflex of a neonate who is the subject. In the case where the grasp reflex is very weak or cannot be observed, for example, there is suspicion of serious brain injury or upper spinal cord lesion. Namely, screening for an abnormality of the cerebral nervous system can be performed in conjunction with congenital heart disease screening by monitoring of the arterial oxygen saturation.

The optical sensor may further comprise: a sound outputting section which is configured to output predetermined sound. Preferably, the predetermined sound is sound which suppresses excitement of a neonate who is the subject.

According to the above configuration, a body motion of the subject who is a neonate can be suppressed, and the contactness between the grasping member and the hand can be maintained. Also in the case where the subject of pulse oximetry is a neonate, therefore, it is possible to suppress a measurement error from occurring.

The optical sensor may further comprise: a wireless communicating section which is configured to transmit and receive a signal between the light emitter and the light receiver, and an external apparatus.

In this case, the optical sensor may further comprise: a calculating section which is configured to perform a calculation process on a signal communicated between the light emitter and the light receiver, and the wireless communicating section.

According to the above configuration, a cable which connects the optical sensor to the external apparatus can be omitted. It is possible to avoid a situation such as that a cable is tangled with the subject by an unexpected motion. Also in the case where the subject of pulse oximetry is a neonate, therefore, it is possible to suppress a measurement error from occurring.

The light emitter and the light receiver may be supported by a member having a light shielding property.

According to the above configuration, light other than that emitted from the light emitter can be prevented from entering the light receiver from the outside. Also in the case where the subject of pulse oximetry is a neonate, therefore, it is possible to suppress a measurement error from occurring.

What is claimed is:

1. An optical sensor comprising:
   a light emitter;
   a light receiver;
   a rod-shaped grasping member in which one of the light emitter and the light receiver is disposed, the rod-shaped grasping member including a curved circumferential surface configured to be grasped by a hand of a subject; and
   a clamping member which is adapted to clamp a part of the hand of the subject between the clamping member and the rod-shaped grasping member, another one of the light emitter and the light receiver being disposed in the clamping member,
   wherein the clamping member extends in a longitudinal direction of the rod-shaped grasping member, and
   wherein the clamping member and the rod-shaped grasping member are arranged such that the part of the hand of the subject is insertable between the clamping member and the rod-shaped grasping member in a direction intersecting the longitudinal direction of the rod-shaped grasping member.

2. The optical sensor according to claim 1, further comprising: a scattering layer which is placed in an optical path of light emitted from the light emitter.

3. The optical sensor according to claim 1, wherein the light emitter is disposed in one of the grasping member and the clamping member so that light emitted from the light emitter passes through a plurality of fingers of the subject when the plurality of fingers is placed between the grasping member and the clamping member.

4. The optical sensor according to claim 3, further comprising: a light shielding member provided between the grasping member and the clamping member and adapted to be disposed between the plurality of fingers when the plurality of fingers is placed between the grasping member and the clamping member.

5. The optical sensor according to claim 1, further comprising: a belt member, wherein one end of the belt member is fixed to one of the grasping member and the clamping member, and a part of the belt member is attachable to and detachable from the other of the grasping member and the clamping member.

6. The optical sensor according to claim 5, wherein the part of the belt member is variable.

7. The optical sensor according to claim 1, wherein the grasping member has a shape of a rotating body.

8. The optical sensor according to claim 1, wherein a positional relationship between the light emitter and the light receiver is constant.

9. The optical sensor according to claim 1, wherein at least a part of the grasping member is flexible.

10. The optical sensor according to claim 9, wherein
    the grasping member includes a first portion in which at least a thumb and index finger of the subject are to be placed, and a second portion in which at least one of the light emitter and the light receiver is disposed,
    the first portion is higher in rigidity than the second portion, and
    the second portion is higher in flexibility than the first portion.

11. The optical sensor according to claim 1, wherein an outer circumferential surface of the grasping member includes a recess having a shape which is adapted to receive a part of a right hand of the subject.

12. The optical sensor according to claim 1, further comprising: an indicator guiding grasping by the right hand of the subject.

13. The optical sensor according to claim 1, further comprising: a sensor which is configured to detect a state change of at least a part of the grasping member, the change being due to a grasping pressure exerted by the subject.

14. The optical sensor according to claim 1, further comprising: a sound outputting section which is configured to output predetermined sound.

15. The optical sensor according to claim 1, further comprising: a wireless communicating section which is configured to transmit a detection signal from the light receiver to an external apparatus and to receive a control signal for the light emitter from the external apparatus.

16. The optical sensor according to claim 15, further comprising: a calculating section which is configured to perform a calculation process on the detection signal and the control signal.

17. The optical sensor according to claim 1, wherein the light emitter and the light receiver are supported by a member having a light shielding property.

\* \* \* \* \*